United States Patent [19]

Gadbois

[11] Patent Number: 5,347,877
[45] Date of Patent: Sep. 20, 1994

[54] STORM WATER RUNOFF FIRST FLUSH SAMPLER

[75] Inventor: Laurence E. Gadbois, West Richland, Wash.

[73] Assignee: The United States of America as represented by the Secretary of the Navy, Washington, D.C.

[21] Appl. No.: 125,008

[22] Filed: Sep. 21, 1993

Related U.S. Application Data

[63] Continuation of Ser. No. 919,350, Jul. 23, 1992, abandoned.

[51] Int. Cl.$^5$ ............................................. G01N 1/00
[52] U.S. Cl. ................................................. 73/863.52
[58] Field of Search ........... 73/863.02, 863.31, 863.41, 73/863.51, 171, 170 R, 49 T, 863.51; 215/307-309; 232/41 R, 43.1, 43, 43.5; 141/324, 331; 220/366-374; 137/571

[56] References Cited

U.S. PATENT DOCUMENTS

| | | |
|---|---|---|
| 1,742,400 | 1/1930 | Larsson . |
| 2,388,548 | 11/1945 | Jurs, Jr. . |
| 2,398,828 | 4/1946 | Gray ..................... 137/571 |
| 2,707,399 | 5/1955 | Rice ..................... 73/863.51 |
| 2,781,941 | 2/1957 | Lindsay ................. 220/372 |
| 3,826,144 | 7/1974 | Wessels . |
| 4,205,710 | 6/1980 | Dunicz .................. 141/331 |
| 4,245,499 | 1/1981 | Nguyen et al. ......... 73/171 |
| 4,494,585 | 1/1985 | Waldecker ............. 141/331 |
| 4,495,951 | 1/1985 | Kenda ................... 73/864.51 |
| 4,532,813 | 8/1985 | Rinehart . |
| 4,638,920 | 1/1987 | Goodhues, Jr. ........ 73/49.2 T |
| 4,880,156 | 11/1989 | Wallet .................. 232/43.1 |
| 4,928,541 | 5/1990 | Toom et al. . |
| 4,958,528 | 9/1990 | Garrison . |
| 5,110,553 | 5/1992 | Ruschak et al. ........ 73/863.51 |

FOREIGN PATENT DOCUMENTS

| | | | |
|---|---|---|---|
| 540792 | 5/1957 | Canada ................................ | 141/331 |
| 2003869 | 5/1973 | Fed. Rep. of Germany ...... | 137/571 |
| 2245980 | 4/1974 | Fed. Rep. of Germany ...... | 137/571 |
| 2250809 | 4/1974 | Fed. Rep. of Germany ...... | 137/571 |
| 110256 | 9/1925 | Switzerland ........................ | 141/331 |

Primary Examiner—Robert Raevis
Attorney, Agent, or Firm—Harvey Fendelman; Thomas Glenn Keough; Michael A. Kagan

[57] ABSTRACT

A storm water runoff first flush sampler is provided which includes at least one container which has a top and a bottom. A water collection device is also provided which has an inlet end for collecting water and an outlet end for discharging the collected water. The inlet end of the water collection device is located above the top of the container, and the outlet end of the water collection device opens into the container for filling the container with water. A device is also provided for venting air from the container as it is filled with water and discharging the vented air at a level above the top of the water collection device. This arrangement enables automatic termination of gravity flow to the container when water reaches the level of the water collection device. Also, the water collection device is provided with an aperture that releases the kinetic pressure resulting from water falling onto the inlet end of the water collection device, thereby preventing alteration of the composition of the original sample by additionally collected water. Further, the liquid collection device has a P trap which will prevent sediment from additional runoff water from entering the container after the container is full.

14 Claims, 4 Drawing Sheets

STORM WATER RUNOFF FIRST FLUSH SAMPLER

This is a continuation of application Ser. No. 07/919,350, filed Jul. 23, 1992, now abandoned.

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The invention relates to a device and method for sampling the first flush of runoff water from a storm or simply sampling any liquid discharge where a pure sample of the discharge is required.

The first flush of storm water runoff is typically the most chemically contaminated and poses the greatest environmental risk as compared to subsequent flows. Accordingly, the need is becoming more apparent by association with the problem or by government regulation to obtain the first flush of storm water runoff so that chemical and toxicological characteristics can be made for monitoring and risk assessment purposes. Many samples may be necessary to characterize the flows contributing to a discharge stream to assess multiple discharge sites.

Measuring runoff is more difficult than measuring point source discharges due to episodic flows and flow-variant chemical concentration. Currently, equipment primarily designed for continuous point source discharges have been adapted for use in nonpoint source monitoring. Typical commercial samplers used to measure runoff are microprocessor controlled to draw a sample through an intake tube inserted in the discharge stream. The problems are numerous. The surface film is not included in the sample. For near source sampling, slow solubility kinetics result in a discharge stream that is not chemically homogeneous, and especially in the case of hydrophobic chemicals, such as nonpolar organics, most of the contaminant mass can occur as a surface film. Under very contaminated conditions, the water may not be able to dissolve the contaminant loads so that even at far downstream sites mid water column samples are biased in their representation of the true contaminant flux. Many sites must be sampled. Of course, large numbers of commercial water samplers or large work crews with "jars in hand" could be employed. Obviously, this is cost prohibitive and there is a need for a low cost and easy to use sampler for obtaining a true sample of the first pulse of storm water runoff.

SUMMARY OF THE INVENTION

The invention provides a very efficient storm water runoff first flush sampler and sampling method. One of the primary features of the invention is that the sampling will automatically terminate very shortly after a container is full, thereby ensuring that the sample is unaltered by subsequent runoff. The following sampling functions are automatically terminated: (1) gravitational flow to the container, (2) flow to the container due to kinetic force impingement of subsequent runoff, and (3) flow of sediment to the container due to subsequent runoff. These important features are obtained with a device and method which is simple to make, simple to use and low in cost. The present invention obtains these features by providing a unique combination of elements. A closed container is provided which has a top and a bottom. A water collection device is also provided which has an inlet end for collecting water and an outlet end for discharging the collected water. The inlet end of the water collection device is located above the top of the container, and the outlet end of the water collection device opens into the container for filling the container with water. A device is also provided for venting air from the container as it is filled with water and discharging the vented air at a level above the top of the water collection device. This arrangement enables the automatic termination of gravity flow to the container. Accordingly, the container will take on substantially no more water after the venting device is filled with water to the level of the inlet of the water collection device. In a preferred embodiment of the invention the water collection device has an aperture between its inlet and outlet ends to release kinetic pressure due to water impinging on the water collection device after the container is fully. This preserves the original sample by preventing additional runoff water from being driven into the container. Further, the water collection device may have a P trap between the aperture and its outlet end which will trap and prevent sediment from entering the container after the container is full. This will prevent the first flush sample filling the container from being altered by sediment, if any, from a subsequent runoff. The invention includes other unique arrangements as well as various methods for accomplishing the desired sampling function.

OBJECTS OF THE INVENTION

An object of the invention is to overcome the aforementioned problems associated with prior art samplers.

Another object is to provide a simple device and method for sampling a liquid discharge which will automatically prevent alteration of the sample even though the liquid discharge continues after the sample is obtained.

A further object is to provide a simple device and method for sampling a liquid discharge which will automatically terminate gravitational flow, kinetic energy flow, and sediment flow to a container shortly after the container is filled with a liquid sample.

Still another object is to provide a simple device and method for obtaining a true sample of the first flush from storm water runoff.

Still a further object is to provide a reliable device and method for obtaining the first flush from storm water runoff in a container and which, without any ancillary inputs of energy, will automatically terminate the following flows to the container shortly after the container is filled with the desired sample: (1) gravitational flow of the runoff water; (2) kinetic flow of the runoff water; and (3) sediment flow.

Yet another object is to provide a device, as set forth in the previous object, which is low in cost, easy to assemble and disassemble and simple to use in the field.

Yet a further object is to provide a device, as set forth in the previous object, which is easily adaptable for obtaining multiple samples in multiple containers.

Still another object is to provide a device as set forth in the previous object which can be easily mounted and removed from a storm sewer grating.

These and other objects of the invention will become more readily apparent from the ensuing specification when taken together with the drawings.

DESCRIPTION OF THE PREFERRED EMBODIMENTS

Figure 1:
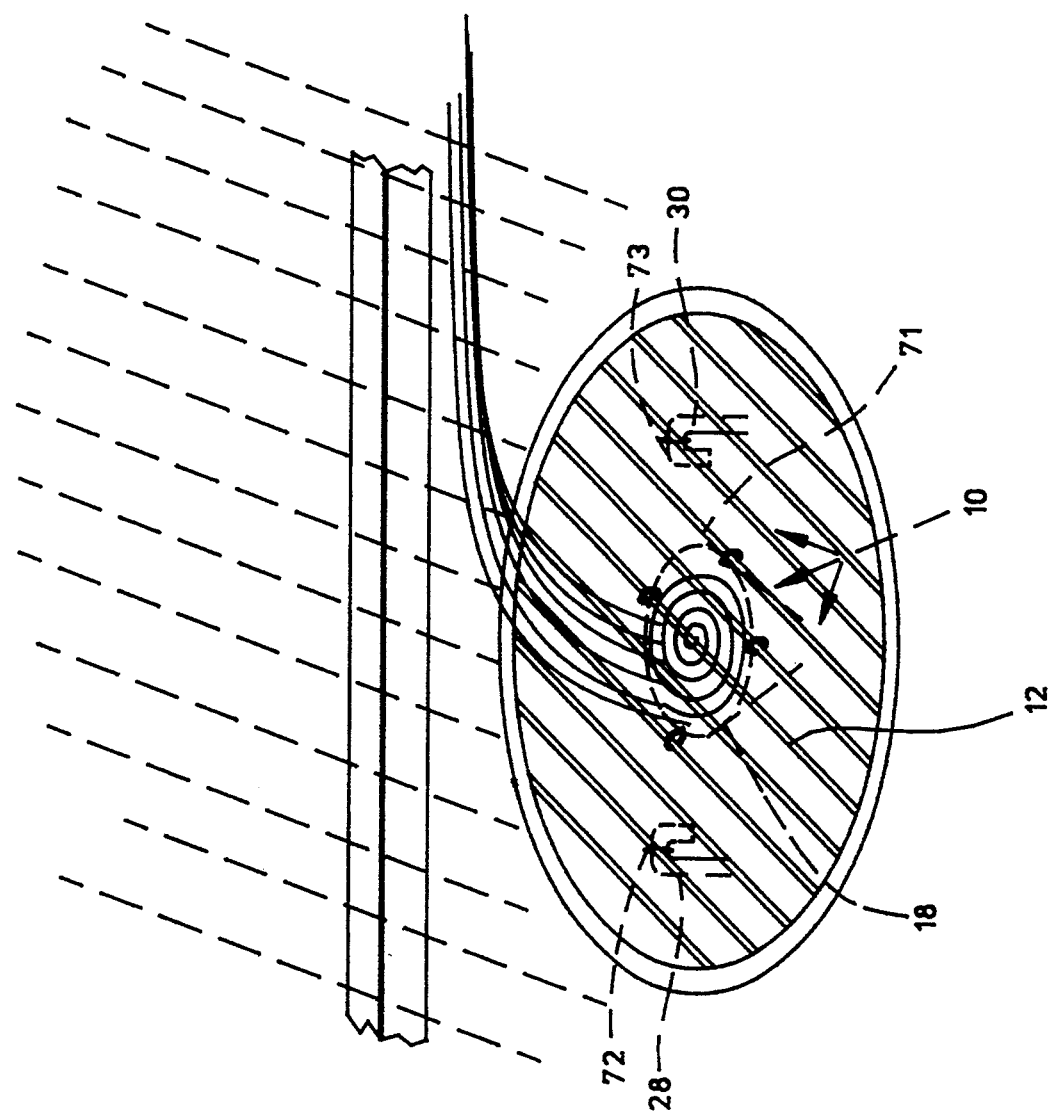
FIG. 1 is an isometric view showing the invention mounted below a storm sewer grating so as to collect water runoff from a storm.
Figure 2:
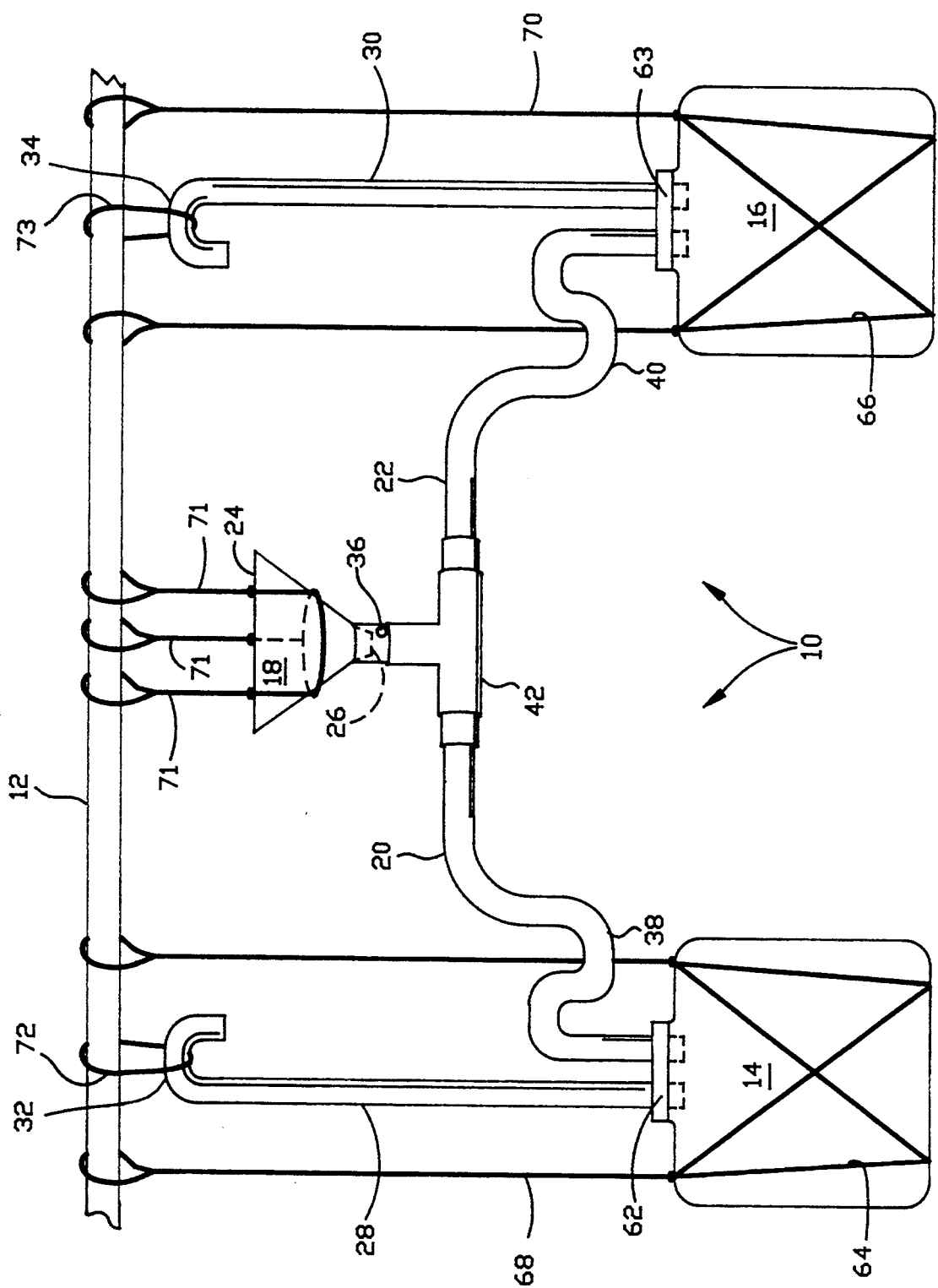
FIG. 2 is a side view of the invention mounted to a storm sewer grating

Referring now to the drawings where like numerals designate like or similar parts throughout the several views there is shown in FIGS. 1 and 2 a sampler 10 which is mounted to the bottom of a storm sewer grating 12 for collecting the first flush of storm water runoff passing through the grating. The sampler 10 may include a pair of closed containers 14 and 16, each container having a top and a bottom. There is also provided liquid collection means having an inlet end for collecting liquid and an outlet end for discharging the collected liquid.

The liquid collection means may include a funnel 18 and a pair of tubes 20 and 22. As shown in FIGS. 1 and 2 the funnel 18 has a large open top intake end 24 for collecting water and a small open bottom discharge end 26 for discharging the water. One end of each tube 20 and 22 is connected to a respective container 14 and 16 and means, which will be described in detail hereinafter, may be provided for connecting the other ends of the tubes to the small bottom discharge end 26 of the funnel. With this arrangement storm water runoff collected by the funnel will flow directly to the containers 14 and 16.

Means are also provided for venting air from the containers 14 and 16 as they are filled with water. This means may include a second pair of tubes 28 and 30. One end of each of these tubes is connected to a respective container 14 and 16 for venting air therefrom as the containers fill with water, and each tube is adapted to extend above the large top intake end 24 of the funnel for discharging the vented thereabove. As shown in FIG. 2, when the funnel 18 is mounted a short distance below the grating 12 the free end portions 32 and 34 of the tubes can be easily positioned to attain this higher elevation. This arrangement provides an important feature of the invention. When the containers are full and the water has risen in the tubes 28 and 30 to the level of the top of the funnel 18 gravitational flow of water to the containers 14 and 16 automatically ceases without the requirement of any ancillary energy inputs. This then ensures that the original samples obtained by the containers 14 and 16 will not be altered by gravitational flow to the containers due to subsequent storm water runoff.

The liquid collection means, as described hereinabove, has an aperture 36 for bleeding additional water collected shortly after the containers 14 and 16 are full, namely when the water reaches a level in the tubes 28 and 30 which is at the top level of the funnel 18. This arrangement provides another important feature of the invention. When the storm continues after the containers 14 and 16 are full there is a kinetic energy impingement of the additional water on the water already resting in the funnel 18. This causes a downward force tending to drive additional water into the containers which would alter the composition of the already obtained first flush sample. This potential problem is overcome by the aperture 36 which releases kinetic pressure due to the additional falling water impinging on the large intake end 24 of the funnel 18, thereby bleeding the downward thrust of water from the system. It is desirable that the aperture be below the bottom discharge end 26 of the funnel because this is the location of the kinematic head release of the water.

The liquid collection means, described hereinabove, may also be provided with means between the aperture 36 and the containers 14 and 16 for trapping sediment shortly after the containers 14 and 16 are full of water. This may be accomplished by providing each tube 20 and 22 with a respective dip or P trap 38 and 40. This arrangement provides still a further important feature of the invention. Shortly after the containers 14 and 16 are full of the desired first flush of storm water runoff, namely when water in the vent tubes 28 and 30 has reached the top level 24 of the funnel 18, additional water falling into the funnel from a continuing storm will deposit undesirable sediment which would alter the composition of the already obtained samples. The P traps 38 and 40 trap this sediment and prevent it from reaching the containers 14 and 16. It should be understood, however, that the original sample of each container will include a representative amount of sediment which passed through the P traps 38 and 40 while the containers were being filled with the first flush of storm water runoff.

Figure 3:
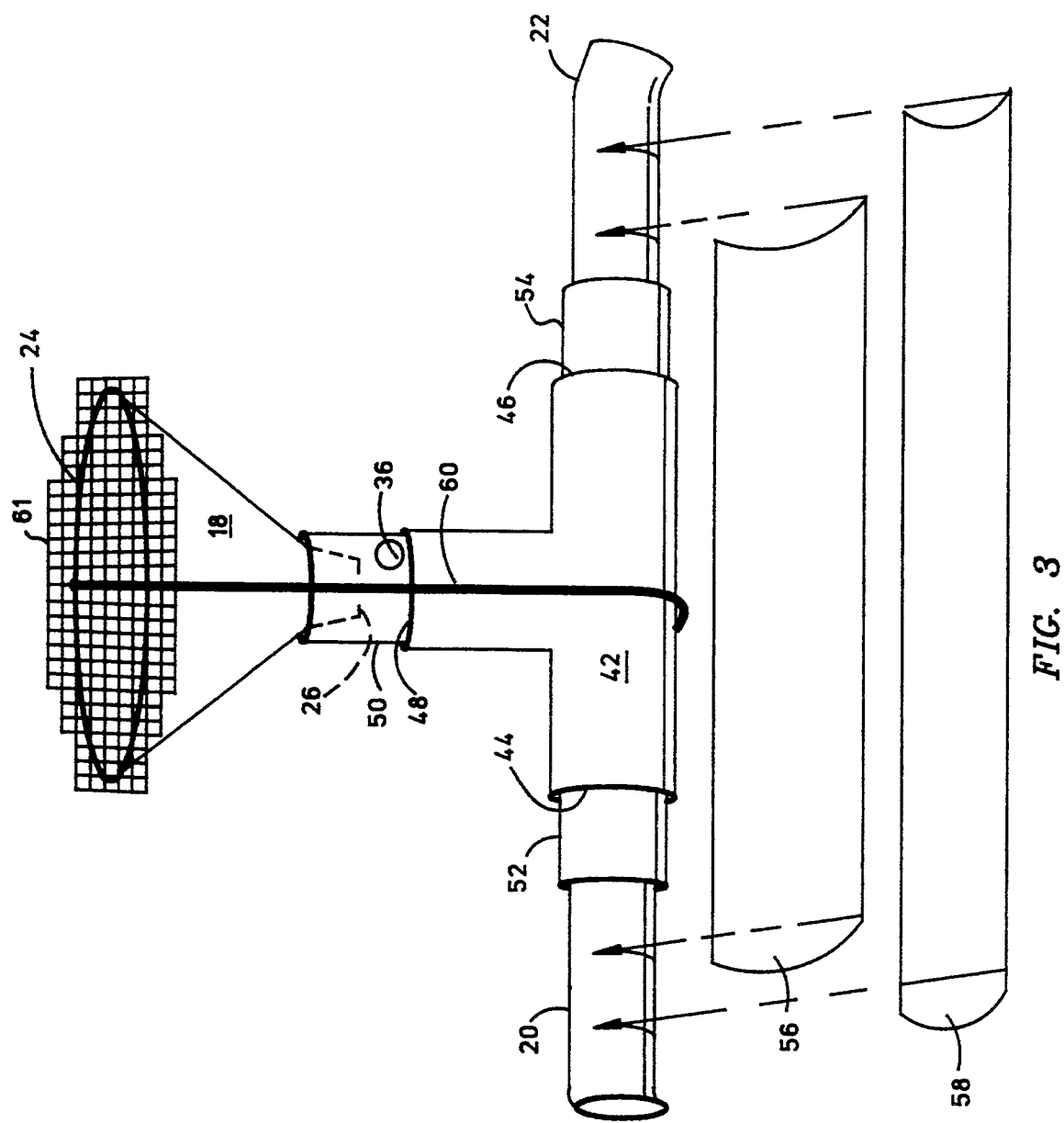
FIG. 3 is an enlarged portion of FIG. 2, shown in isometric, to illustrate various details of the invention.

An exemplary connecting means for the funnel 18 and the tubes 20 and 22 are best illustrated in FIG. 3. The connecting means may include a T coupling 42 which has feed through ends 44 and 46 and a perpendicular end 48. The small bottom discharge end, or neck end, 26 of the funnel 18 may be connected to the perpendicular end 48 of the T coupling by any suitable means, such as a bushing 50. With this arrangement the aperture 36 can conveniently be provided in the bushing 50 at a location below the bottom end 26 of the funnel. The top end of each tube 20 and 22 may be connected to a respective feed through end 44 and 46 of the T coupling by any suitable means, such as bushings 52 and 54. The bushings 50, 52 and 54 may be simply cut from plastic pipe to the required lengths and of a size to provide a snug fit between the elements to prevent leakage. If desired, retention of the tubes 20 and 22 to the T coupling 42 may be assured by wrapping a double thickness of aluminum foil 56 to the bottom of these components followed by a slightly longer piece of duct tape 58 over the aluminum foil and sticking to the tubes 20 and 22 beyond the T coupling. Additional connecting means may include a cord 60 which extends over the top end 24 of the funnel, about the bottom end of the T coupling 42 and which is tied at some location (not shown) to secure these components, and yet provide for a quick release. Under the cord 60 and on top of the funnel 18 it is desirable to place a screen 61 with a mesh slightly smaller than the internal diameter of the tubes 20 and 22 and any internal orifice for stopping debris which could plug the system. This screen may be provided with openings for the cord to pass through so that the screen can appropriately extend laterally beyond the top end 24 of the funnel. It is important that the portion of the cord over the top of the funnel be kept clean. This may be accomplished in the field by aluminum foil and plastic wrap (not shown) over the screen, and removing it just prior to the sampling operation.

As shown in FIG. 2, the tubes 20 and 22 and the tubes 28 and 30 are connected to the tops of the respective containers 14 and 16. It is desirable that the ends of these tubes extend a short way into the containers. The containers may have openings in respective screw-on caps 62 and 63 for receiving the tubes. The openings in the caps should be slightly smaller than the outside diameters of the tubes so that a snug fit will ensure a good seal therebetween.

For sampling water runoff from a storm it is most desirable that the sampler 10 be mounted to and below a storm sewer grating 12. An exemplary mounting means, shown in FIG. 2, includes various elements. Saddles 64 and 66 may be provided for respective containers 14 and 16 with support ropes or straps 68 and 70 which may be conveniently tied to the crossbars of the grating 12. Small ropes 71 may be wrapped or looped about the bottom of the funnel 18 and tied to the crossbars of the grating so that the top 24 of the funnel 18 is located a short distance therebelow. The outer end portions 32 and 34 of the vent tubes 28 and 30 can be tied under the crossbars of the grating 12 with small ropes 72 and 73 so that the outer end portions or ends thereof are above the top end 24 of the funnel.

It should be noted that the above arrangement lends itself to utilizing a plurality of containers which exceeds the pair described hereinabove. The only difference would be that the T coupling 42 would be replaced with a coupling having additional ports. Further, the sampler may be used to collect liquids other than storm water runoff. For instance, the sampler could be mounted to collect free falling rain water or could be used to collect liquid discharges from pipes and still be within the spirit of the invention.

Figure 4:
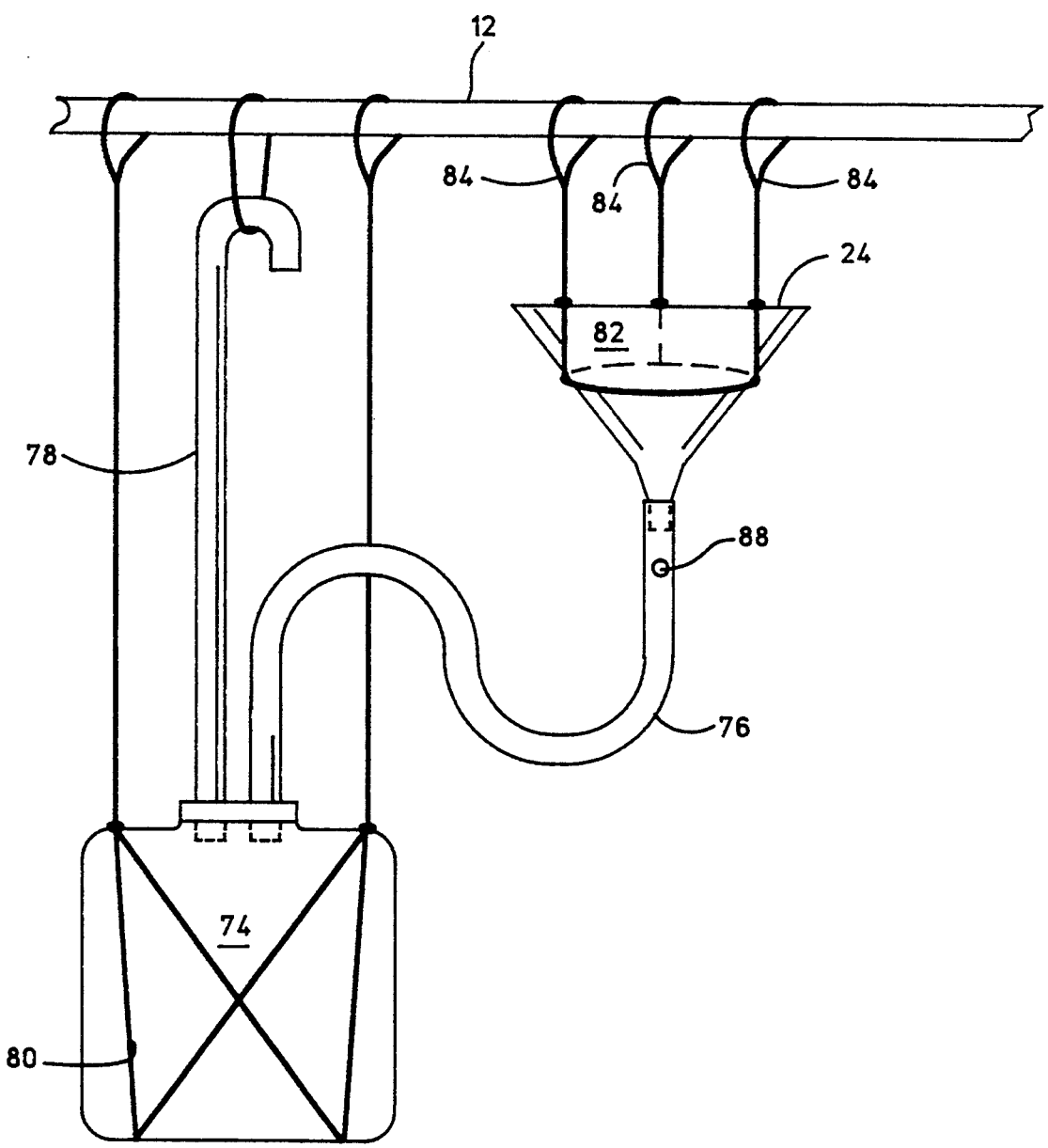
FIG. 4 is a side view of another embodiment of the invention mounted to a storm sewer grating.
Figure 5:
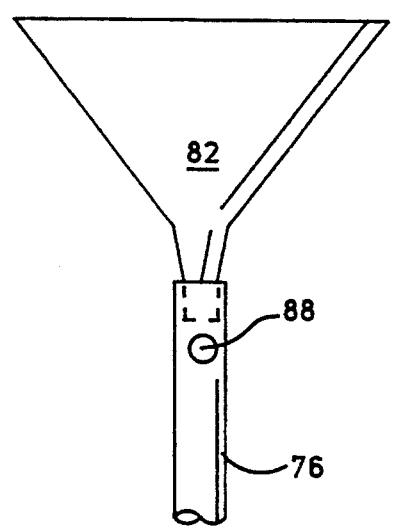
FIG. 5 is an enlarged portion of FIG. 4 showing various details of the invention.

As shown in FIG. 4, the invention may simply include one container 74, one flow tube 76, one vent tube 78, one saddle 80, along with a funnel 82 and a small rope 84 for tying the funnel 82, all of the same type as shown in the embodiment described hereinabove (see FIGS. 1 and 2). The one container embodiment would be mounted to the grating 12 in the same manner. The only difference for the one container embodiment is that a top portion of the tube 76 is connected to the bottom of the funnel 82 and the tubing would be provided with an aperture 88 which serves the same purpose as the aperture 36 in the first embodiment. As shown in FIG. 5, the tubing 76 can have an internal diameter which fits snugly over the bottom portion (neck portion) of the funnel to provide a good seal. The aperture 88 in the tubing 76 should be below the bottom of the funnel 82 so as to provide a kinematic head release when additional water falls (impinges) on water in the funnel after the container 74 is full. This will keep the original sample obtained in the container 74 from being altered by subsequent runoff. Accordingly, the same automatic features are obtained as with the first described embodiment, namely termination of the following when the additional runoff continues after the vent line 78 is filled to the top level of the funnel 82: (1) gravity flow of water to the container; (2) kinetic energy driven flow of water to the container; and (3) sediment flow to the container.

It is important that the containers of any embodiment be constructed from an inert material, such as Teflon, since the samples may reside therein for some time before analysis. Of lesser importance the tubing should be constructed from an inert material. The tubing may be either flexible or rigid as desired.

There are so many embodiments of the invention that the breadth of the invention can only be envisioned from several methods of practice. In reference to FIG. 4, one such method may include positioning the container 74 below a water runoff area, transmitting runoff water in a substantially contained, captured or closed fashion from a water collection position above the container 74 to the container 74, such as by the funnel 82 and the tube 76; and venting air from the container to a position above the water collection position, such as by the vent tube 78. With this arrangement, soon after the container 74 is filled with water no more runoff water can enter the container. The method may also include releasing kinetic pressure from a location between the water collection position (top of funnel 82) and the container 74 when runoff water continues after the container is full, such as by the aperture 88. The method may further include trapping sediment between the water collection position and the container 74 when water runoff with sediment continues after the container is full so as to prevent the additional sediment from altering the originally obtained sample.

OPERATION OF THE INVENTION

The operation of the invention will be described for the embodiment shown in FIGS. 2 and 3, however, it should be understood that the operation would be similar for other embodiments envisioned. Prior to mounting the sampler 10 all of the components should be connected, namely the flow tubes 20 and 22 connected to the funnel 18 and the containers 14 and 16, the vent tubes 28 and 30 connected to the containers 14 and 16 and the screen 61 in place with the cord 60 therearound for retention of the screen to the funnel 18 and the funnel to the T coupling 42. Optionally plastic wrap and aluminum foil (not shown), in that order, can be placed and wrapped over the screen to prevent intrusion of debris or undesired water prior to the sampling. The wrap and foil can be left on even after mounting the sampler until just before the prospect of a storm, at which time it can be easily removed. To mount the sampler 10 the straps 68 and 70 and the small ropes 71 are tied to crossbars of the grating 12 with the funnel 18 in a position to collect runoff water and with each of the tubes 20 and 22 provided with a dip to form P traps 38 and 40. Each of the vent tubes 28 and 30 are tied to a respective crossbar of the grating by small ropes 72 and 73 so that a portion of each of the tubes is above the top 24 of the funnel.

When a storm takes place the first flush of the runoff water will fill both containers 14 and 16. Shortly thereafter the vent tubes 28 and 30 will fill with water until the water reaches the top level 24 of the funnel. At this time gravitational flow of water to the containers 14 and 16 will cease. Subsequent runoff water impingement on water already in the funnel will exert a downward kinetic force tending to drive water into the containers 14 and 16 even though gravitational flow has ceased. Downwardly driven water will be prevented from entering the containers by the aperture 36 which will release kinetic pressure, thereby bleeding the downward thrust of water from the system. Further, the sediment that is deposited in the funnel due to subsequent runoff will be prevented from reaching the containers 14 and 16 because of the P traps 38 and 40. However, if the first flush of runoff water contained sediment the original sample will contain a representative sediment content which was passed through the P traps 38 and 40 during the filling of the containers. Accordingly, the unique arrangement of the invention will prevent alteration of the first flush of runoff water by subsequent runoff. After the samples have been obtained the sampler 10 is removed from the grating 12 making sure that the P traps 38 and 40 are not elevated to allow sediment to slide down into the containers. The sampler is of such low cost that it can be discarded after use or optionally can be easily cleaned for further use.

Obviously, many modifications and variations of the present invention are possible in light of the above teachings. It is therefore to be understood that within the scope of the appended claims, the invention may be practiced otherwise than as specifically described.

What is claimed is:

1. A liquid sampler having an interior and an exterior, an upstream end near a source of fluid discharge, and a downstream end comprising:
   a closed container generally positioned at the downstream end, having a top and a bottom;
   liquid collection means generally positioned at the upstream end, having an inlet end for collecting liquid and an outlet end for discharging the liquid, the inlet end having an inlet opening, the outlet end having an outlet opening, the inlet opening being larger than the outlet opening;
   a fluid conduit having an open inlet end for receiving the liquid from the collection means and an open outlet end for discharging the liquid into the container, said fluid conduit having a conduit sidewall, said sidewall having means for releasing kinetic pressure due to falling liquid impinging on the collection means after the container is full of the liquid, and for providing a discharge directly to the exterior of the sampler of liquid impinging on the collection means after the container is full of the liquid, said means for releasing and providing a discharge comprising an aperture located downstream of the collection means outlet opening; and
   means for venting air from the container as it is filled with liquid and discharging the vented air at a level above the top of the liquid collection means;
   whereby the container takes on no more liquid after the venting means is filled with liquid to the level of the inlet of the liquid collection means.

2. A liquid sampler as claimed in claim 1 wherein:
   the fluid conduit includes a P trap between the aperture and the outlet end for trapping and preventing additional sediment from entering the container after the container is full;
   whereby sediment content of the original sample filling the container is prevented from being altered by the presence of subsequent liquid at the inlet end of the liquid collection means.

3. A liquid sampler as claimed in claim 1 wherein the liquid collection means comprises a funnel.

4. A liquid sampler as claimed in claim 3 wherein:
   the venting means comprises a tube which has an air intake end connected to the container and an air discharge end which is located above the funnel.

5. A liquid sampler as claimed in claim 4 including:
   means for mounting the liquid sampler to a fixed structure with the funnel located above the top of the container.

6. A first flush liquid sampler having an interior and an exterior and having an upstream end near a source of liquid discharge and a downstream end comprising:
   a plurality of containers generally positioned at the downstream end, each container having a top and a bottom;
   a funnel generally positioned at the upstream end having a large open top intake end for collecting liquid and a small open bottom discharge end for discharging the liquid;
   a fluid conduit having an open inlet end for receiving the liquid from the funnel and an open outlet end for discharging the liquid into the containers, said fluid conduit having a conduit sidewall, said sidewall having means for releasing kinetic pressure due to falling fluid impinging on the funnel after the containers are full of the liquid and for providing a discharge directly to the exterior of the sampler of liquid impinging on the funnel after the containers are full of the liquid, said means for releasing and providing a discharge comprising an aperture located downstream of the small open bottom discharge end of the funnel; and
   a set of discharge tubes, one end of each discharge tube being connected to one of the plurality of containers for venting air therefrom when the respective container fills with liquid and the other end of each tube extending above the large top intake end of the funnel for discharging the vented air.

7. A liquid sampler as claimed in claim 6, wherein:
   the fluid conduit includes at least one P trap located between the funnel and the respective container for trapping and preventing additional sediment from entering the container after the container is full of liquid;
   whereby sediment content of the original sample filling the container is prevented from being altered by the presence of subsequent liquid at the top intake end of the funnel.

8. A liquid sampler as claimed in claim 7 wherein:
   the plurality of containers comprises two containers;
   the fluid conduit includes a T coupling coupled to the funnel; and wherein the fluid conduit further comprises:
   first and second tubes each having one end thereof connected to a respective end of the T coupling.

9. A liquid sampler as claimed in claim 8 including:
   a screen over the large top intake end of the funnel;
   a cord extending over the top of the screen and around the bottom of the T coupling for retaining the screen to the top of the funnel and the funnel to the T coupling and yet enabling a quick release of the elements.

10. A liquid sampler as claimed in claim 9 wherein:
    the fluid conduit and the set of discharge tubes are connected to the containers through the tops of the containers.

11. A liquid sampler as claimed in claim 10 including:
    means for mounting the sampler to a fixed structure with the large top end of the funnel being located above the top of the container and with the other end of the tubes being located above the top end of the funnel.

12. A liquid sampler as claimed in claim 11 wherein the mounting means includes:
    a saddle for each container which has support cords for attachment to the fixed structure.

13. A method of sampling the sediment content of first runoff liquid comprising the steps of:
  positioning a container below a liquid runoff area;
  transmitting runoff liquid in a substantially closed fashion from a liquid collection location above the container to the container;
  venting air from the container to a location above the liquid collection location;
  trapping and preventing additional sediment from entering the container after the container is full of said first runoff liquid; and
  releasing kinetic pressure from a location between the liquid collection location and the container when liquid runoff continues after the container is full;
  whereby additional liquid due to runoff subsequent to the first runoff is prevented from entering the container.

14. A method as claimed in claim 13 including:
  trapping sediment between the kinetic pressure releasing location and the container when liquid runoff with sediment continues after the container is full so that this additional sediment will not enter the container to alter the original sample contained therein.

* * * * *